United States Patent [19]
Rucker

[11] 4,178,364
[45] Dec. 11, 1979

[54] ART OF SHAVING

[76] Inventor: Jimmy Rucker, 400 E. 33rd St., Apt. 1401, Chicago, Ill. 60616

[21] Appl. No.: 603,145

[22] Filed: Aug. 8, 1975

[51] Int. Cl.$^2$ ........................... A61K 7/15; B26D 7/08
[52] U.S. Cl. ............................................. 424/73; 83/22
[58] Field of Search ............................... 424/73; 83/22

[56] References Cited
U.S. PATENT DOCUMENTS

| | | | |
|---|---|---|---|
| 3,314,857 | 4/1967 | Fainer | 424/73 |
| 3,715,942 | 2/1973 | Courtney | 424/73 X |
| 3,808,920 | 5/1974 | Fisher | 424/73 X |

*Primary Examiner*—Dale R. Ore
*Attorney, Agent, or Firm*—George F. Lee

[57] ABSTRACT

A method of shaving hair from the human body with a razor wherein the skin area after washing is wet with water and the edge of the razor is wet with a water repellant organopolysiloxane fluid such as dimethyl polysiloxane.

2 Claims, 8 Drawing Figures

ART OF SHAVING

This invention relates to the art of shaving with a razor. Although the invention has particular utility in removing facial beard growth, it has general application to removing hairs from other parts of the body as well.

A principal object of the invention is the elimination of razor pull in shaving and the consequent discomfort and other effects thereof.

In shaving with a razor, the resistance of the hairs to the cutting edge of the blade as well as the resistance of the skin to movement of the blade edge thereacross has long been a matter of concern. Much effort has gone into developing means and method for perfecting the cutting edge of the razor blade. To this end new metal compositions have been devised for the blade itself which would better take and/or longer hold a sharpened edge. Also new honing methods have been devised to produce the sharpened edge. In recent years numerous coating materials and methods of their application to the blade and its edge have been developed in an effort to assure maintenance of the sharp edge of the razor blade, to protect it from corrosion or other attack during extended storage and from degradation with repeated use. Such coating materials have varied from precious metals and their alloys to polymerized resins, as well as incompletely cured resins which retain a gel-like character. Examples of these cross-linked and partially cured resins have included various silicones and halogenated hydrocarbons, polyolefins such as polyethylene, polytetrafluoroethylene and polyperfluoropropylene. Several of these coated blades have been produced commercially and some have enjoyed a degree of consumer acceptance.

Conventionally, the beard or other portion of the body from which hairs are to be shaved is prepared by first washing the skin area to remove soil, etc., and then applying a shaving cream, lotion or high lathering soap to set up the hairs and/or by softening the hairs to decrease their resistance to the cutting edge of the razor. The cream or soap was also considered to have a lubricating effect as the razor edge was drawn across the skin.

However, particularly among those persons subject to *pseudofolliculitis barbae*, these advances in the art have been of little comfort and the problem has persisted. Actually it appears that the problem of *pseudofolliculitis barbae* has been only aggravated by conventional shaving practices thus far discussed.

Thus, a second and equally important object of the invention is to devise a method of shaving which will achieve a close shave look when practiced regularly, but without the attendant problem of *pseudofolliculitis barbae* which is prevalent among males with curly beards who shave regularly.

In accordance with this invention, the art of shaving has been simplified by eliminating the need of shaving creams and soap and utilizing two liquid phases, one of which is applied to the razor edge and the other of which is water is applied to the face or other skin area to be shaved. Because the first phase which adheres to the razor edge is immiscible and repellant to the water, a low frictional interface is established between two liquid phases and the razor edge is able to follow closely the contours of the skin but with little or no resistance wherefore the razor cuts cleanly and with little pull.

Referring to the drawings:

FIG. 1 schematically illustrates straight hair growing out of a straight follicle;

FIG. 2 schematically illustrates curly hair as it grows out of a highly curved follicle;

Figure 1:
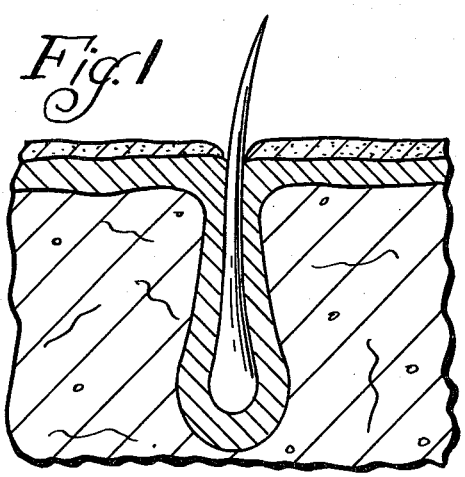
Figure 2:
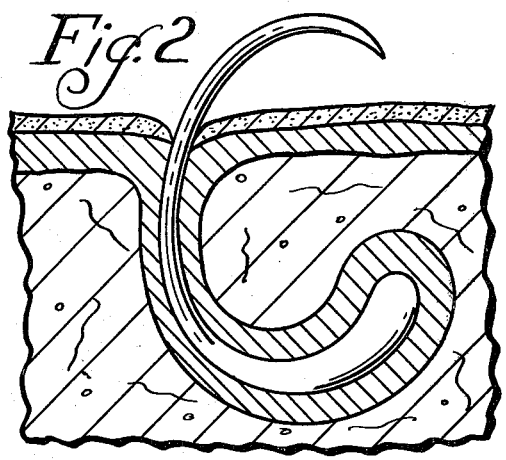

Referring more particularly to the several views comprising the drawing and first to FIGS. 1 and 2, growing hair wherever it occurs, whether on the face, under the arm or elsewhere on the body, tends to follow the shape of the follicule out of which it grows. Thus straight hair grows out of a straight follicule as illustrated by FIG. 1. Wavy hair grows out of a slightly curved follicule; and curly hair grows out of sharply curved follicules as, for example, illustrated by FIG. 2. Although not restricted thereto, sharply curved hair follicules are prevalent among the black adult male population who are therefore particularly susceptible to *pseudofolliculitis barbae* as a consequence of regular shaving.

Figure 3:
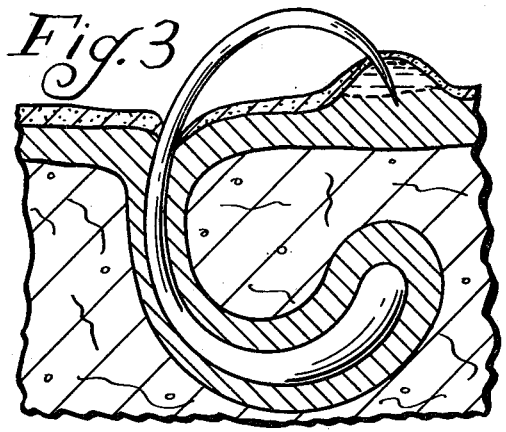
FIGS. 3 and 4 illustrate two forms of ingrown hair or *pseudofolliculitis barbae* to which people with curly hair are often subjected as a consequence of regular close shaving.
Figure 4:
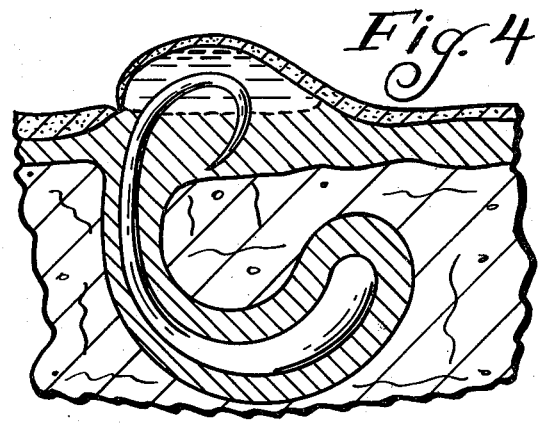
Figure 5:
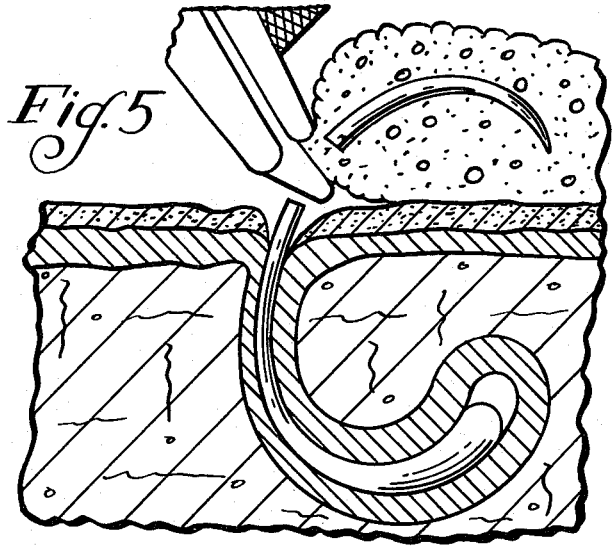
FIG. 5 illustrates the displacement of the hair within its follicle which the razor causes in a conventional method of shaving using a lathered soap or shaving cream on the face and is believed to be one cause of *pseudofolliculitis barbae*.
Figure 6:
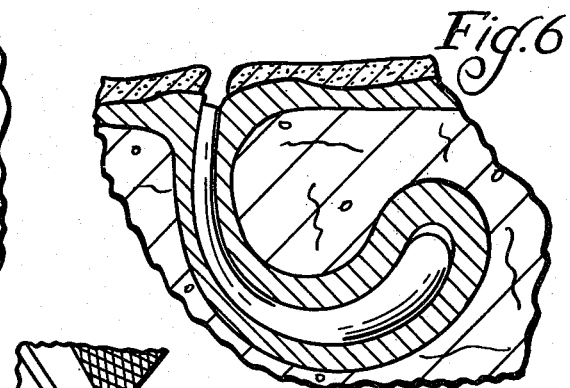
FIG. 6 illustrates schematically how the pulled hair may retreat into the follicule when cut by the razor so that its cut end lies below the skin line.
Figure 7:
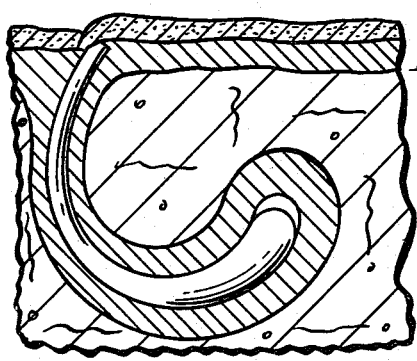
FIG. 7 illustrates the path which the cut hair may thereafter take as it grows.

In *pseudofolliculitis barbae*, the hairs as they grow out of the follicule have a tendency to turn or curve inwardly back toward the skin, penetrating the same and precipitating an inflamatory reaction (FIGS. 3 and 4). Shaving regularly with a razor where the beard is prepared by lathering the face with soap or cream appears to promote the *pseudofolliculitis barbae*. This is believed to be due to the fact that when the razor cut occurs at a distance from the follicule, the hair is left with a sharp point which can readily penetrate the skin with further growth of the hair forming a papule as illustrated in FIG. 3. Where the cut of the razor occurs close to the follicule, because the hair has been partially out of its follicule, as illustrated by FIG. 5, the remaining end of the hair retreats into the follicule below the outer skin level as illustrated by FIG. 6. As the hair commences to grow, because of its sharply curved trajectory the hair may turn on an arc without ever exiting from beneath the skin line as illustrated by FIG. 7. This precipitates an inflammatory reaction in the form of so-called pustules as illustrated by FIG. 4. The papules and pustules which thus develop can be extremely painful and so much so that many black males elect to grow a beard rather than to contend with the problem of ingrown hair.

I, however, have found that the problem of *pseudofolliculitis barbae* can be considerably reduced if instead of lathering the face with shaving cream or soap I apply only water to the face but wet the razor edge with an organo-polysiloxane fluid which is water repellant.

Figure 8:
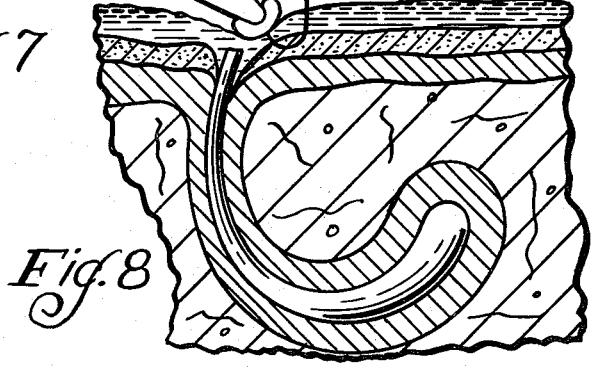
FIG. 8 illustrates a shaving method according to the present invention.

While the explanation therefor is not yet fully understood, it is believed that when shaving in this manner there is less pull on the hairs due to the lowered frictional resistance at the organo-polysiloxane fluid-water interface which results from the non-polar characteristic of the organo-polysiloxane. In a conventional shaving process the soap or shaving cream acts to reduce the surface tension of the water and this is relied upon to soften the hairs and thereby to decrease their resistance to the sharpened razor edge. In accordance with this invention, the hairs are not softened to the same extent. However, the razor edge is able to slide smoothly and with minimal frictional resistance across the face or other skin area because of the sharply defined interface a that exists between the water phase b which adheres to the face and the water repellant phase c (organo-polysiloxane fluid) which adheres to the razor edge (FIG. 8). Thus the razor edge cuts both cleanly and also close to the skin surface with minimal or no pull on the hair. Because the razor edge is able to move rapidly across the water wet skin area, the hairs present less resistance and razor pull is reduced. The hairs being cut close to the skin line tend to be blunted and because the hairs are not being pulled out of their follicules their cut ends remain above the skin level. At least in experience to date, the problem of *pseudofolliculitis barbae* has been considerably reduced.

The organo-polysiloxane fluid of choice is an alkyl polysiloxane fluid such as dimethylpolysiloxane fluid having a viscosity of 350 to 1000 centistokes. If the viscosity is too light the organo-polysiloxane tends to wash away and a further coating of the razor edge therewith may be required. If it is much heavier than 1000 centistokes, the coating tends to clog. A viscosity of 600 to 700 is to be preferred; best results to date have been obtained where the razor edge is coated with a mixture comprising equal parts of a dimethylpolysiloxane such as SF-96 (350) having a viscosity of 350 centistokes (25° C.) and a longer chain dimethylpolysiloxane such as SF-96(1000) having a viscosity of 1000 centistokes (25° C.) Such alkyl polysiloxanes are essentially inert, non-volatile as well as odorless and colorless, are water insoluble and have a surface tension of 21.1 dynes/cm.

In shaving according to the invention, any of the presently commercially available razor blades of which I am aware, coated or uncoated, may be utilized. The face or other skin area is prepared by first thoroughly washing to remove all soil and other contaminants. The face is then left wet or is re-wet with water. The razor is then prepared by spreading a drop of the alkyl polysiloxane fluid along the edge of its blade. No shaving cream, lotion or agent other than water is applied to the face, although under some circumstances a small quantity (perhaps 3 to 5% by weight) of carboxy polymethylene (Carbopol) may be added to the water to improve its "cling".

In accordance with this invention, a sharp line of cleavage is defined between the water layer and the second phase represented by the water repellant alkyl polysiloxane fluid which facilities relatively friction free movement of the razor edge across the face. The temperature of the water is therefore not critical and it may be warmed or not according to the comfort and needs of the user. Neither is it necessary that the razor edge be wet with water. Because the alkyl polysiloxane fluid is water insoluble, no harm is done if the blade edge is cleaned with water during the shaving process. Actually, this may be desirable: - to remove the cut hairs which tend to collect in the thin coating of alkyl polysiloxane. Because the invention is predicated on establishing a near friction-free interface between two liquid phases, depending on the speed with which the shaving act is conducted, it may be desirable to re-wet the face during the shaving act. Because both fluid phases are colorless and transparent, the shaving action is not obscured as in conventional shaving when an opaque soap lather or shaving cream is used. The shaver is able to see what he is doing and therefore obtain a closer or more complete shave. This feature of being able to view the shaved area is of particular advantage when shaving an area of the body as in preparation for surgery.

In addition, because of the thickness of water on the skin and the thickness of alkyl polysiloxane on the razor edge represent two mutually repellant colorless phases, not only does one get a cleaner, closer shave in accordance with the invention, but the razor edge as it glides smoothly over the face is also able to closely follow the contours thereof and with little or no pull.

From the aforesaid description it will be apparent that the recited objects, advantages and features of the invention have been demonstrated as obtainable in a highly practical manner and by a method which is uncomplicated and convenient to practice.

Having described my invention, I claim:

1. A method of shaving with a razor in which the skin is first washed clean and wet with water to provide a colorless transparent first liquid phase over the clean skin area from which the hair is to be shaved with the razor, spreading a drop of water-immiscible fluid consisting of a mixture of dimethyl polysiloxanes having a viscosity of 600 to 700 centistokes across the length of the razor edge to produce a trasparent colorless second liquid phase which adheres to the razor edge and is repellent to the first liquid phase, and moving the dimethyl-polysiloxane-coated razor edge across the water-wet area of the skin, a sharply defined low frictional interface being created between the two liquid phases such that the razor edge slides smoothly across the skin in the shaving act and cuts cleanly close to the skin with minimal pull on the hair and frictional resistance between the skin and the razor edge.

2. Method of shaving as claimed in claim 1 wherein the fluid with which the razor edge is wet consists of equal parts of dimethyl polysiloxane fluid having a viscosity of 350 centistokes and dimethyl polysiloxane fluid having a viscosity of 1000 centistokes.

* * * * *